United States Patent
Jones

(10) Patent No.: US 9,861,089 B2
(45) Date of Patent: Jan. 9, 2018

(54) PROTECTIVE HOOF COATING AND TRIMMING METHOD FOR PREVENTION OF HOOF DAMAGE AND INFECTION

(71) Applicant: David Thomas Jones, Bechtelsville, PA (US)

(72) Inventor: David Thomas Jones, Bechtelsville, PA (US)

( * ) Notice: Subject to any disclaimer, the term of this patent is extended or adjusted under 35 U.S.C. 154(b) by 141 days.

(21) Appl. No.: 14/961,746

(22) Filed: Dec. 7, 2015

(65) Prior Publication Data

US 2017/0156302 A1 Jun. 8, 2017

(51) Int. Cl.
*A01L 15/00* (2006.01)
*A61K 31/785* (2006.01)
*A61K 9/00* (2006.01)

(52) U.S. Cl.
CPC ............ *A01L 15/00* (2013.01); *A61K 9/0017* (2013.01); *A61K 31/785* (2013.01)

(58) Field of Classification Search
None
See application file for complete search history.

(56) References Cited

U.S. PATENT DOCUMENTS

| | | | |
|---|---|---|---|
| 3,682,179 A * | 8/1972 | Firth | A61D 9/00 206/582 |
| 4,182,340 A * | 1/1980 | Spencer | A01L 3/00 606/212 |
| 6,231,972 B1 * | 5/2001 | Fryer | A01L 15/00 428/343 |
| 2012/0309864 A1 * | 12/2012 | Ruppert | A61L 27/16 523/115 |
| 2013/0209812 A1 * | 8/2013 | Gorodisher | C09D 179/04 428/458 |
| 2017/0037275 A1 * | 2/2017 | Johnston | C09D 135/02 |

* cited by examiner

*Primary Examiner* — Daniel J Colilla

(57) ABSTRACT

A protective coating for an ungulate hoof comprising an abrasive-resistant, anti-microbial adhesive that is harder and more flexible than a hoof wall applied to the ground-contacting surface of a hoof and the dorsal hoof wall for the purpose of furnishing protection against hoof damage and hoof infection and adding support to a hoof.

2 Claims, No Drawings

PROTECTIVE HOOF COATING AND TRIMMING METHOD FOR PREVENTION OF HOOF DAMAGE AND INFECTION

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO SEQUENCE LISTING, A TABLE OR A COMPUTER PROGRAM

Not applicable.

BACKGROUND OF THE INVENTION

1. Field of the Invention

The present invention relates to animal husbandry (119) and in particular to a protective hoof coating and a trimming method to prevent hoof damage.

2. The Description of Prior Art

The attempted prevention of damage to livestock hooves dates back at least 5,000 years. Any domesticated animal used for work had to remain sound to be useful. More than anything, foot lameness was the limiting factor on how much work could be done by oxen, horses, mules, donkeys, camels, etc. When traveling, the distance covered was directly impacted by the limitation of the draft animals' feet. Prevention of foot soreness was a very practical endeavor and livelihoods, sometimes survival, depended on the results. Someone who did a better job of protecting their animals' feet from damage had an economical advantage over others.

The ancient Egyptians and others made pads of woven grass and reeds or made leather boots and strapped them on the feet of their camels and horses to limit wear. Generally, conditioning of the hooves remained adequate until the fourth century. Extensive research has shown a correlation between an invention of war and the necessary invention of more serious foot protection. It was around 331 B.C. that the first use of caltrops was documented. Caltrops were small star shaped metal objects that, when strewn on a battle field, always landed with a point up. This proved lethal to horses, oxen, camels, elephants or men. It punctured the sole and caused immediate foot damage and lameness and was often the deciding factor on winning the battle. It was around that time that the Greeks, Romans and Celts began metal hoof protection. The "hipposandal" protected the entire sole and was first bronze then later iron strapped on the hoof with leather thongs. Typically, this was only used in circumstances that required such extreme sole protection. The first evidence of iron shoes for horses, oxen and goats that were fastened with nails can be traced to the $5^{th}$ or $6^{th}$ century and attributed to Celtic blacksmiths. Samples of these first shoes were wide and covered almost the entire sole as befitted the need for protection against caltrops.

It was later that the development of horseshoes took a wrong direction. Previously, hoof protection for horses covered the entire bottom of the hoof and allowed the sole, hoof wall and frog to all be ground-bearing surface. While metal shoes for oxen and goats continued to support the entire foot, horseshoes developed into the form we see today where only the hoof wall is supported. Suspending the sole of a horse has caused innumerable problems by putting too much weight on the hoof wall and has led to numerous inventions to repair the damaged hoof wall.

The split hoof clamp described by Wiestner (U.S. Pat. No. 381,868) objects to the rigidity of previous inventions which interferes with horses and cattle hooves' natural expansion, which horseshoes also do. Wiestner does not address the cause of the hoof crack.

Bane (U.S. Pat. No. 3,118,449) describes patching a quarter crack by removing the healthy hoof wall material behind the crack and nailing on a shoe that has been shortened so as to not put pressure on the damaged area of the hoof. Bane says that race horses have weak hooves and are prone to hoof wall cracks and "seedy toe" (which I will address later). These can become infected and cause more damage if not treated with antibiotics by a veterinarian. This process is still suspending the sole by use of a horseshoe which puts excessive stress on the hoof wall.

Firth, et al. (U.S. Pat. No. 3,682,179) describes a flexible mesh patch for hoof wall cracks used in conjunction with a urethane resin. Firth says that the resin should be flexible to match the hoof's elasticity. Although not claimed, Firth also describes the use of the resin over the entire dorsal surface of the hoof to protect against brittleness from moisture loss or to rebuild seriously damaged hooves. A urethane resin would not be tough enough to protect the hoof, nor rigid enough to aid in supporting the hoof wall without the use of the other hoof structures. Firth does not address the root cause of the crack.

Spencer (U.S. Pat. No. 4,182,340) describes threading over a hoof crack and filling it with adhesive material. The drawings show a horseshoe, the adhesive requires that one can nail through it, and there is no mention of any type of trimming to structurally remediate the crack.

Stovall (U.S. Pat. No. 5,681,350) describes a rigid and permeable prosthesis for when a hoof wall is debrided. Stovall states that, "the hoof wall is the most important weight-bearing structure of the foot". Research has shown that the sole and frog are the more important weight-bearing structures of the hoof, as written in "Physiological Trimming for a Healthy Equine Foot", Dr. Robert Bowker, VMD, PhD in the Journal of Equine Veterinary Science, July 2003. Stovall also states, "Anatomically, the hoof wall is analogous to the claws of a cat or the toe nails of man". That would appear to make the horse the only domestic animal we force to walk on its toenails, which is not structurally sound.

Fryer (U.S. Pat. No. 6,231,972), my previous invention, describes an adhesive used as a protective hoof coating. However, the coating is described as being used primarily in place of a horseshoe and used only to protect the ground contacting hoof wall surface. There is little mention of protecting the other ground contacting surfaces of the sole and frog. Also, the trim method therein is described as dependent on the endeavor the horse is to be used for rather than the horse's natural conformation as the present invention describes.

BRIEF SUMMARY OF THE INVENTION

My previous invention (Fryer, U.S. Pat. No. 6,231,972) was before certain research by veterinarians and 15 years of my own observations and experimentation in so-called "barefoot horses". The previous invention described an adhesive coating designed to replace rigid horseshoe in form and function, placed only on the ground-contacting surface of the hoof wall. Since then I and other researchers have found that horseshoes mounted to the hoof wall thereby suspending the hoof sole and frog are not adequately supportive of the weight of the horse. This is a cause of hoof wall damage which the prior art attempts to repair but which the present invention prevents. An adhesive coating in place of rigid horseshoes or rubber boots is still advantageous because there is nothing to fall off, and that it strengthens the hoof rather than weakens it. However, the present invention expands those improvements both in method of use and preventive capabilities for damage and infections in ways never before thought possible until now. The preferred embodiment describes the optimum hoof conformation utilizing a protective hoof coating comprising an anti-microbial agent combined with a trimming method which I will describe in detail resulting in the prevention of most hoof damage.

BRIEF DESCRIPTION OF THE SEVERAL VIEWS OF THE DRAWING

Not applicable.

DETAILED DESCRIPTION OF THE INVENTION

The first horse, Eohippus, was a small dog-sized mammal walking on a padded solar cushion with four toes in the front and three in the back, very similar to today's dogs and cats. The toes had small "proto-hooves" similar to a dogs, but walked on the pads of the toes. Eohippus evolved to Mesohippus with three toes in the front and hind, but similar in the weight-bearing pads and small proto-hooves. Mesohippus evolved to Dinohippus which had one main weight-bearing toe and two outer vestigial toes. As the outer toes became vestigial they lost the proto-hooves and the middle toe developed into more of a defined hoof structure. Dinohippus evolved into Equus which is the modern horse we know today. Equus walks on one toe with a developed hoof wall but still with a padded solar cushion (frog) which looks remarkably similar to the main foot pad of a dog or cat.

The frog of a horse, similar to the pad of a dog paw, is tough yet resilient and designed for shock absorption. Expansion of the frog is necessary for circulation, pumping blood up the lower leg where there are only ligaments and tendons with no muscles to return blood up the leg. All other hooved animals: cattle, goats, camels, pigs, etc. have a tough horny covering on their toes, yet walk on their padded solar regions. The horse has not evolved differently.

The earliest hoof protection as described in the prior art covered the entire bottom of the hoof and utilized all hoof components for support. When horseshoes were invented, approximately 1,000 years ago, they started out mostly as wide as the bottom of a hoof as seen in historic findings. While metal hoof protection nailed to the bottoms of oxen and goats remained the same, supporting the entire foot, horseshoes then evolved into narrow strips of metal covering only the bottom of the hoof wall. The result of this is to support only the hoof wall while suspending the hoof sole and frog. It becomes the only hooved animal expected to walk entirely on its toenails. Structurally, instead of positioning the weight of the bony column of the leg directly above the support, it makes the hoof function like a toilet plunger, with the pressure on the periphery. When a horseshoe is fastened which restricts the expansion motion at the ground surface, the hoof wall has to expand around the middle of the wall like a toilet plunger causing undue pressure and potential damage. The effect of this places the entire weight of the horse (and rider) on the hoof wall and causes damage such as hoof wall cracks, splayed hooves and "seedy toe" where the laminae is stretched and the hoof wall separates at the toe. The nails of a horseshoe further weaken the hoof structure already overloaded for its design. The plethora of inventions for repair of hoof wall cracks is evidence of the extent of the problem.

My previous invention (Fryer, U.S. Pat. No. 6,231,972) described hoof protection primarily for the bottom of the hoof wall and was designed to replace a rigid horseshoe. Observation of successes I had of also applying hoof protection to the sole convinced me that a different direction of experimentation was required. Observations of the underside of feral (mustang) hooves showed thick callused hooves which ground contacted more completely than domestic horses. Studies done by research veterinarians found that all the components of the bottom of the hoof should be ground-contacting and weight-bearing similar to a feral hoof. The question remained of how to create that type of hoof in a domestic horse? A feral horse's hooves are shaped and develop tough thick calluses naturally by travel over varied terrain as many as 30 miles a day. Domestic horses are typically restricted in their travels and have weaker hooves. How can a domestic horse's hooves become thicker and stronger?

Because I realized that many domestic horses suffer from stone bruising of the sole and not the hoof wall while obviously mustangs don't, I concentrated my research on protecting the sole more than the hoof wall. I found that the adhesive hoof protection prevented wear of the sole and allowed the sole to grow thicker. I developed a different method of hoof trimming which primarily trimmed the excess hoof wall but did not trim the sole thinner, unlike most trimming methods. The thicker sole was better protection against stone bruising, similar to walking over stones wearing boots versus only socks. A thicker, tougher layer between the stones and the sole's sensitive tissue showed less sensitivity to stones and the protective coating prevented damage. The adhesive protective coating prevents wear of the ground-bearing components, the hoof wall, sole and frog, allowing them to develop to the point where they equally distribute the weight of the animal's leg. Meanwhile, applying the adhesive over the top edge of the hoof wall prevents wear of the toe and sides of the hoof.

The other advantage of applying the adhesive protective coating on the sole and dorsal surface of the hoof wall concerns moisture in the hoof. Research has shown that a healthy hoof has 25% moisture in the hoof wall and up to 50% in the hoof sole. The dorsal surface of the hoof is naturally protected by the periople, a thin clear layer which grows out with the hoof wall and protects the outer hoof wall like a varnish. It retains moisture in all climate conditions, wet or dry. When this periople is removed by rasping or penetrated by nail holes it can lose moisture, the hoof can dry out and more easily develop cracks. The present invention's protective coating seals the moisture in the hoof wall in all climate conditions, like the periople. It also keeps the proper moisture level in the sole promoting healthy sole growth. Rubber hoof boots, on the other hand trap moisture against the hoof which softens and weakens the hoof keratin.

An object of the present invention concerns the goal of what the hoof should look and function like as a result of the proper application of the hoof protective coating of the present invention. The ideal foot of any hooved animal should be as nature intended through ages of evolution— shaped by wear on the ground. However, domestic animals are typically restricted in their travel and must be trimmed to maintain that foot shape.

There is no point to applying a hoof protective coating to help grow a better hoof only to have it trimmed off by improper trimming methods. Trimming the hoof of a horse is similar to trimming the hoof of any hooved animal. In all cases the entire ground-contacting componentry of the hoof should be used to distribute the weight of the animal. In the case of a horse, the hoof sole, the bottom of the hoof wall and the frog should equally distribute the weight of the horse. That way no one hoof component is overloaded and subject to damage from either hoof cracks or rotation of the coffin bone if laminitis occurs. In the case of laminitis, if the coffin bone is supported from below, it cannot rotate or drop downward and will prevent the severe damage of the lameness known as "founder". Trimming in this simple proper fashion will follow the natural conformation of the individual hoof and not try to form an artificial hoof for particular endeavors. Cloven hooved animals should be trimmed to ground level. Any hoof growth that extends under the hoof can trap bacteria and cause hoof rot.

Essentially, the proper trimming technique from the inverted horse hoof view is: trim the hoof wall level with the hoof sole and rasp the entire ground-bearing surface flat and rasp any sharp edges so they feel rounded. Do not carve out the hoof sole. This simple technique will balance the sole to the ground and will match the natural conformation of the hoof. All hoof components will share the weight of the horse. Cloven hooved animals are similar in that the hoof claw should be trimmed to ground-bearing level so it is not weight bearing or grown under the hoof.

The adhesive coating formula of my original invention (Fryer, U.S. Pat. No. 6,231,972) has been improved both by ingredients and method of use. The original formula comprised mostly an epoxy resin and a curing agent with aramid fibers. In the present invention, the epoxy formulation developed used is a formula commonly used in food containers, so it is non-toxic. Adding a natural, anti-microbial formula cure accelerator is an improvement in two areas.

The first improvement in the present invention is that it accelerates the curing rate. This causes increased shrinkage which, when applied to the entire ground-bearing surface of the hoof and also up onto the lower dorsal surface of the hoof wall, will furnish some support to the hoof, similar to a polymer boot. This is an important feature when the hoof is transitioning from the effects of previously having horseshoes applied. The restrictive nature of horseshoes tends to weaken the hoof and blood flow is restricted. When the horseshoes are removed, often the horse is sore immediately thereafter due to increased expansion of the hoof. The shrinking effect of the rapidly curing adhesive protective coating will lend some support and help make the horse more comfortable. In the longer term, it restricts the amount a hoof will splay as it grows longer, and helps keep it more in conformation.

The second improvement in the present invention is due to the anti-microbial properties of the cure accelerator. The hoof of a horse is susceptible to many types of infections, notably thrush and White Line Disease. Thrush is a bacterial infection in the commissures on either side of the frog. White Line Disease is an infection that attacks the laminae on the inner side of the hoof wall and causes a separation of the tissue. This is particularly difficult to access as it is under the horn of the hoof wall and not available for topical treatment without debriding the hoof wall and further exposing the hoof to infections. A study by Cornell University College of Veterinary Medicine found that White Line Disease can be caused by any of over 40 different bacteria, molds or fungi or a combination thereof. The bacteria can be either aerobic, anaerobic or both and therefore very difficult to treat. The adhesive protective coating of the present invention with its anti-microbial formula not only prevents infections, but has been used alone to successfully treat thrush, White Line Disease and even toe nail canker in a zoo elephant. The coating seals off aerobic bacteria and disinfects anaerobic bacteria.

An advantage of the present invention is that the coating is harder than a hoof wall, generally about 85 Shore D hardness, yet more flexible than a hoof. This coating will protect better than other available hoof patch materials that are acrylic or urethane. The present inventions protective coating also prevents "graveling" where a foreign object such as a small stone penetrates into the white line. Because the weight of the animal is on the hoof, the object cannot move downward and must move upward under the hoof wall. Because the hoof wall is tough, the object moves upward until it finds a soft spot to come out, typically at the coronary band. This graveling opens up a hole under the hoof wall where infections can intrude and cause White Line Disease. The exit of the object also leaves a horizontal crack at the coronary which must grow out as the hoof grows down. This adhesive protective coating applied over the white line of the hoof will prevent penetration of foreign objects. Applied over the horizontal crack it will prevent infection and keep the crack from expanding.

The preferred embodiment of the present invention is to first prepare the hoof by trimming in the previously described method so that the primary weight-bearing components are directly under the bony column of the leg and, as much as possible, there is no undue weight pressure on any single component. An adhesive protective coating is then applied to all areas intended as ground-bearing surfaces and approximately one inch onto the dorsal surface of the hoof, basically forming an adhesive boot. This coating comprises a non-toxic epoxy resin formulated as a coating rather than a bonding agent that is harder and more flexible than a hoof wall, a rapid-set curing agent, aramid pulp fibers and an anti-microbial cure accelerator. The adhesive protective coating is dispensed from a two-part cartridge and mixed through a mixing nozzle attached to the end of the cartridge. Once adequately dispensed, it is spread over the hoof with either a spatula or a glove. In addition, the adhesive protective coating can be applied over any damaged areas of the hoof wall such as cracks, rasp marks and nail or screw holes. The coating can then be covered with a powder such as talc before the hoof contacts the ground to prevent smearing before curing. The goal of this procedure is to protect all ground-bearing components of a hoof as they develop to distribute the weight of the animal's leg over all components. Continuation of the above embodiment will prevent most hoof damage and infections.

While the above description contains detailed specifications and instruction, these should not be construed as limitations on the scope of the invention, but rather as an exemplification of one preferred embodiment thereof. Many other variations are possible, such as different adhesive formulations or different methods of application such as an aerosol spray. Accordingly, the scope of the invention should be determined not by the embodiment illustrated, but by the appended claims and their legal equivalents.

What is claimed is:

1. An adhesive, abrasive-resistant protective coating for an ungulate hoof comprising a non-toxic epoxy resin, a non-toxic curing agent, aramid fibers and a Hydroxy Acid, anti-microbial cure accelerator that is harder and more flexible than a hoof wall applied to the ground-contacting surface of a hoof and the dorsal hoof wall for the purpose of furnishing protection against hoof damage and hoof infection.

2. The protective coating of claim 1 whereby the adhesive shrinkage due to the accelerated cure provides support to an ungulate hoof.

* * * * *